US009265818B2

(12) United States Patent
Suarez et al.

(10) Patent No.: US 9,265,818 B2
(45) Date of Patent: Feb. 23, 2016

(54) **GENETICALLY MODIFIED *BABESIA* PARASITES EXPRESSING PROTECTIVE TICK ANTIGENS AND USES THEREOF**

(75) Inventors: Carlos E. Suarez, Pullman, WA (US); Donald P. Knowles, Jr., Pullman, WA (US); Terry F. McElwain, Pullman, WA (US)

(73) Assignees: The United States of America, as represented by the Secretary of Agriculture, Washington, DC (US); Washington State University Research Foundation, Pullman, WA (US)

( * ) Notice: Subject to any disclaimer, the term of this patent is extended or adjusted under 35 U.S.C. 154(b) by 770 days.

(21) Appl. No.: 12/114,988

(22) Filed: May 5, 2008

(65) Prior Publication Data

US 2008/0317786 A1 Dec. 25, 2008

Related U.S. Application Data

(60) Provisional application No. 60/927,800, filed on May 4, 2007.

(51) Int. Cl.

| | |
|---|---|
| *A61K 39/018* | (2006.01) |
| *C12N 1/11* | (2006.01) |
| *A61P 33/02* | (2006.01) |
| *C12N 15/63* | (2006.01) |
| *A61K 39/00* | (2006.01) |
| *C07K 14/435* | (2006.01) |

(52) U.S. Cl.

CPC ........... *A61K 39/018* (2013.01); *A61K 39/0003* (2013.01); *C07K 14/43527* (2013.01); *A61K 2039/523* (2013.01)

(58) Field of Classification Search

None

See application file for complete search history.

(56) References Cited

U.S. PATENT DOCUMENTS

| | | | | |
|---|---|---|---|---|
| 5,587,311 | A | 12/1996 | Cobon et al. | |
| 6,100,501 | A | 8/2000 | von der Heyde | |
| 6,103,758 | A | 8/2000 | Sembo | |
| 6,331,297 | B1 | 12/2001 | Allan et al. | |
| 7,722,860 | B2 * | 5/2010 | Kappe et al. | 424/93.1 |
| 8,124,109 | B2 * | 2/2012 | Kickhoefer et al. | 424/263.1 |
| 2005/0244437 | A1 * | 11/2005 | Van Poppel et al. | 424/269.1 |

OTHER PUBLICATIONS

Suarez et al. Int. J. Parasitol. 34: 1177-1184, 2004.*

Cobon G.S. In: New Generation Vaccines. MM Levine (Ed), Marcel Dekker, Inc., New York, pp. 1145-1151, 1997.*

Skolnick et al. Trends in Biotechnology 18: 34-39, 2000.*

Greenspan et al. Nature Biotechnology 7: 936-937, 1999.*

McGuinnes et al. Mol. Microbiol. 7: 505-514, Feb. 1993.*

McGuinnes et al. Lancet 337: 514-517, Mar. 1991.*

Kuriyama et al. Cell Motility and the Cytoskeleton 30: 171-182, 1995.*

Bendayan M. J. Histochem. Cytochem. 43: 881-886, 1995.*

Fujii et al. J. Protozool. Res. 13: 10-14, 2003.*

Concise Encyclopedia: Biochemistry and Molecular Biology Third Edition, (Ed) Scott TA et al., Walter de Gruyter, New York, p. 489, 1997.*

Kumazawa et al. Mol. Cell Neurosci. 52: 97-105, 2013.*

Waitkus et al. Mol. Cell. Biol. 34: 1800-1811, 2014.*

Willadsen et al. Parasite Immunol. 13: 605-616, abstract, 1991.*

Sharp et al. J. Chrom., 512: 189-202, abstract, 1990.*

Boue , O. et al., "Production and biochemical characterization of the recombinant Boophilus microplus Bm95 antigen from Pichia pastoris," Experimental and Applied Acarology, (2004), vol. 32, pp. 119-128.

Callow, L.L. et al., "Development of Effective Living Vaccines Against Bovine Babesiosis—The Longest field Trial?," International Journal for Parasitology,(1997), vol. 27, No. 7, pp. 747-767.

De La Fuente, Jose et al., "Vaccination against ticks(*Boophilus* spp): the experience with the Bm86-based vaccine Gavac," Genetic Analysis: Biomolecular Engineering, (1999), vol. 15, pp. 143-148.

De Waal, D.T. et al., "Live vaccines against bovine babesiosis," Veterinary Parasitology, (2006), vol. 138, pp. 88-96.

Garica-Garcia, Jose C. et al., "Control of ticks resistant to immunization with Bm86 in cattle vaccinated with the recombinant antigen Bm95 isolated from the cattle tick, Boophilus microplus," Vaccine, vol. 18, pp. 2275-2287.

Latif, A.A. et al., "Naturally Acquired Host Resistance in Tick Control in Africa," Insect Science and its Application, (1992), vol. 13, No. 4, pp. 505-513.

Rand, Keith N. et al., "Cloning and expression of a protective antigen from the cattle tick Boophilus microplus," PNAS Biochemistry, (Dec. 1989), vol. 86, pp. 9657-9661.

Suarez, Carlos et al., "Intergenic regioins in the rhoptry associated protein-1 (rap-1) locus promote exogenous gene expression in Babesia bovis," International Journal for Parasitology, (2004), vol. 34, pp. 1177-1184.

Suarez, Carlos E. et al., "Characterization and gene expression of Babesia bovis elongation factor-1a," International Journal for Parasitology, (2006), vol. 36, pp. 965-973.

Wharton, R.H., "Tick-Borne Livestock Diseases and Their Vectors, 5. Acaricide resistance and alternative methods of tick control," FAO Animal Production and Health Paper, (1983), 36, pp. 33-41.

Willadsen, P. et al., "Isolation from the Cattle Tick, Boophilus Microplus, of Antigenic Material Capable of Eliciting a Protective Immunological Response in the Bovine Host," International Journal of Parasitology, (1988), vol. 18, No. 2, pp. 183-189.

Willadsen, P. et al., "Vaccination with 'Concealed' Antigens for Tick Control," Parasitology Today, (1988), vol. 4, No. 7, pp. 196-198.

Willadsen, P. et al., "Anti-tick vaccines," Parasitology, (2004), 129, pp. S367-S387.

Anonymous, "Immunization against bovine babesiosis. In: Ticks and Tick-Borne Disease Control: A Practical Field Manual," Food and Agriculture Organiztion of the United Nations, (1984), vol. 2, pp. 388-443.

* cited by examiner

*Primary Examiner* — S. Devi

(74) *Attorney, Agent, or Firm* — John D. Fado; David L. Marks; Lesley Shaw

(57) ABSTRACT

The present invention relates to methods for stable transfection of *Babesia* parasites, and for vaccines conferring immunity against parasitic arthropods.

10 Claims, 4 Drawing Sheets

GENETICALLY MODIFIED *BABESIA* PARASITES EXPRESSING PROTECTIVE TICK ANTIGENS AND USES THEREOF

FIELD OF THE INVENTION

The invention relates to vaccines that are protective against parasitic arthropods.

BACKGROUND OF THE INVENTION

Numerous species of arthropods are parasitic, and many play a role in transmission of disease. Indeed, parasitic arthropods and the diseases they transmit are a global problem. Ecto-parasitic arthropods such as, e.g., ticks, mites, flies, fleas, midges, suck blood from their hosts and in the process, can act as vectors for protozoan, rickettsial and viral pathogens. Thus, the presence of ecto-parasitic arthropods is frequently associated with disease.

Among the ecto-parasitic arthropods, ticks are particularly problematic and harmful. Indeed, ticks are second only to mosquitoes as vectors of human disease, both infectious and toxic. Hard ticks (Ixodidae) can transmit human diseases such as e.g., relapsing fever, Lyme disease, Rocky Mountain spotted fever, tularemia, equine encephalitis, Colorado tick fever, and several forms of ehrlichiosis. Additionally, they are responsible for transmitting livestock and pet diseases, including babesiosis, anaplasmosis and cytauxzoonosis.

Because of their ability to transmit diseases to humans and animals, the medical and economic importance of ticks has long been recognized. Economic losses associated with ticks are typically manifest through their adverse effects on their livestock hosts. See e.g., L'Hostis M, Seegers H. (2002) *Vet Res.* 33(5):599-611; Peter, R. J., et al. (2005) *Vet Parasitol.* 132(3-4):205-215. In addition to being disease vectors, blood sucking by large numbers of ticks can cause a loss of blood in the host animal. This, in turn, can result in a reduction in live weight, and may even result in anemia. Still more, multiple tick bites can reduce the quality of hides. Thus, ticks affect the product performance of livestock.

Ticks and tick-borne diseases are important in all domestic animals, but the development and production of innovative tick control methods have been focused primarily on the economically important tick-borne diseases of cattle. Indeed, the tick borne protozoan *Babesia* parasites remain an important limitation for development of cattle industries worldwide. Effective control of *Babesia* and other tick borne diseases will certainly require eradication of the tick vectors as well as vaccination against the *Babesia* parasites.

Given the impact tick infestations can have on livestock, it is not surprising that numerous methods for tick control have been attempted see e.g., U.S. Pat. No. 6,103,758, U.S. Pat. No. 6,331,297, U.S. Pat. No. 6,100,501 and U.S. Pat. No. 5,587,311. Unfortunately however, every method so far developed has shortcomings that limit wide application of the method.

For example, chemical acaricides have traditionally been the first line defense against ticks, and do show efficacy. Unfortunately however, the use of chemical acaricides has numerous drawbacks, including, but not limited to the development of chemical resistant tick strains, the presence of residues in the milk and meat, and harmful effects on the animals being treated, human beings, and the environment (see e.g., Nolan J. (1990) *Parasitol.* 32:145-153; George J. E., et al. (2004) *Parasitology.* 129(7):S353-S366; Wharton, R. H., and Roulston, W. J. (1970) *Annu Rev Entomol.* 15(1):381-405; and U.S. Department of Agriculture. *Agriculture Hand-*

*book, No.* 321. Washington, D.C.: 1967. *Safe Use of Agricultural and Household Pesticides*; p. 65).

Because of the problems associated with use of chemical acaricide products, alternative methods for tick control have also been used and/or tested. For example, resistance to tick infestation varies among individual animals and among different breeds of cattle (see e.g., Latif, A. A., and Pegram, R. G. (1992) *Insect Sci & Appl.* 13:505-513). Therefore, breeding of tick resistant cattle has been attempted (see e.g., Wharton, R. H. (1983) *Wld Anim Rev*, (*FAO*). 36:34-41). However, despite the attractiveness of this approach to tick control, selective breeding for tick resistance is difficult, unpredictable, and time consuming. Indeed, each animal still develops its own level of resistance in response to tick challenge and a wide range of resistance occurs. Resistance can only be tested by exposing the putatively resistant animals to ticks, and then resistance can only be measured in terms of average number of ticks per animal. Thus, development of new resistant breeds is a time consuming process with limited usefulness.

Despite the difficulties associated with breeding resistant livestock strains, the idea of tick resistant animals remains attractive. Therefore, attempts have been made to achieve resistance through vaccination. Indeed, a number of vaccines against ticks and tick-borne diseases have been developed or are in the course of being developed. Vaccines have utilized complex tick extracts to stimulate an acquired immunity (see e.g., Willadsen, P., and Kemp, D. H. (1988) *Parasitol Today.* 4(7):196-198). And, isolated tick proteins such as Bm86, and Bm95 have been used for the production of recombinant vaccines (see e.g., Willadsen, P., et al. (1988) *Int J Parasitol.* 18(2):183-189; Rand, K. N., et al. (1989) Proc Natl Acad Sci USA. December; 86(24):9657-61; García-García, J. C., et al. (2000) *Vaccine.* 18(21):2275-2287; Willadsen P. (2004) Parasitology 129 Suppl:S367-87 Review; and de la Fuente, J. et al. (1999) Genet Anal. 15(3-5): 143-8. Review).

Unfortunately however, widespread use of recombinant vaccines is limited by a number of factors. First, vaccines, recombinant or otherwise, must be produced in large fermentors. Recombinant proteins and/or other antigens must be isolated, typically requiring cumbersome methods, and the isolated antigens may not be completely pure. Furthermore, the vaccines in use today typically require multiple inoculations per year. Even with multiple inoculations, the available vaccines do not achieve 100% efficiency, and so other control measures e.g., the use of acaracides, need to used in combination with the vaccine for full control of the ticks.

Nevertheless, immunity to parasitic arthropods e.g., ticks, is a highly desired form of parasite control. Indeed, what is needed in the art is an effective vaccine that would provide sustained and effective immunological response with a single inoculation. Such a vaccine would avoid the problems associated with acaricide resistance, chemical residues in food and the environment, and the difficulty of breeding tick resistant species for all animal production systems. Fortunately, as will be clear from the following disclosure, the present invention provides for this and other needs.

SUMMARY OF THE INVENTION

In one embodiment, the present invention provides a method for stable transfection of *Babesia* parasites.

Other features, objects and advantages of the invention will be apparent from the detailed description which follows.

BRIEF DESCRIPTION OF THE DRAWINGS

FIG. 1 Illustrates an exemplary construct comprising bsd-gfp fusion cassette in the expression site. In exemplary embodiments the construct comprises a tick antigen gene, e.g., Bm86, fused to the selectable marker bsd-gfp gene in the expression site.

Figure 2:
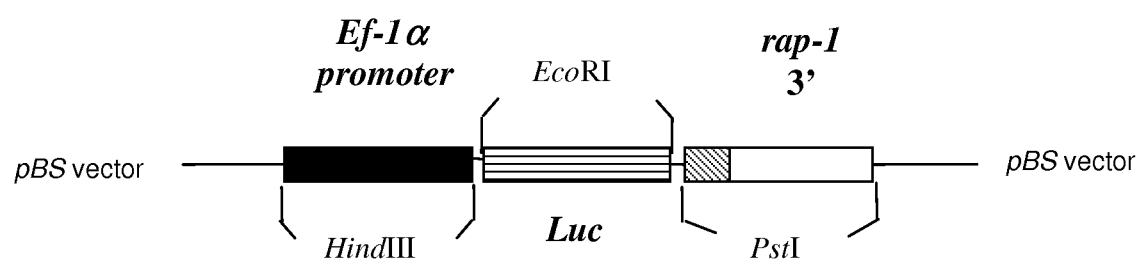

FIG. 2 Illustrates plasmid p4-35 encoding luciferase under the transcriptional control of the *B. bovis* ef-1α promoter.

FIG. 3 A. Transfection of purified *B. bovis* infected red blood cells (iRBC) by nucleofection and electroporation with plasmid p4-35-luc. A. Comparison of luciferase activity in lysates of *B. bovis* transfected with plasmids p4-35-luc or pBS control, using nucleofection (4-35-Am; pbs-am), or electroporation (4-35-BR; pbs-br); "nep-4-35" and "nep-pbs" represent data from non transfected parasites. The luciferase assays were performed 48 hours after transfection. RLU: relative light units. The data in the columns represent the means and standard deviations for RLUs obtained after two independent replicates. B. *B. bovis* percentage of parasitized erythrocytes (PPE) in cultures obtained 24 (blue) and 48 (crimson) hours after transfection with plasmids p4-35-luc or pBS control, using nucleofection (4-35-Am; pbs-am), or electroporation (4-35-BR; pbs-br); "nep-4-35" and "nep-pbs" represent data from non transfected parasites nucleofection or electroporation of iRBC. The data in the columns represent the means and standard deviations for the percentage of parasitized erythrocytes obtained after two independent replicates.

FIG. 4 Structure of plasmid p4-35-ef-luc. The restriction sites used for linearization (KpnI) and double digestion (KpnI and NotI) are indicated with arrows.

DETAILED DESCRIPTION OF THE INVENTION

Definitions

The term "parasitic arthropod" as used herein, refers to arthropods that are parasitic on other species, typically feeding on the blood of their host. Exemplary parasitic arthropods include, but are not limited to ecto-parasitic arthropods e.g., ticks, mites, flies, fleas, midges, etc., Parasitic arthropods are potentially vectors of pathogens and thus can cause disease in animals and man.

The term "tick" as used herein refers to small arthropod arachnids that, along with other mites, constitute the order Acarina. Ticks are ectoparasites, which live by hematophagy on the blood of mammals, birds, and occasionally reptiles and amphibians. Ticks are vectors of a number of diseases, including, but not limited to babesiosis. Major families of ticks include the Ixodidae or hard ticks, which have thick outer shells made of chitin, and Argasidae or soft ticks, which have a membraneous outer surface. A third family, Nuttalliellidae, contains one rare African species, *Nuttalliella namaqua*. Soft ticks typically live in crevices and emerge briefly to feed, while hard ticks will attach themselves to the skin of a host for long periods of time. Tick bites look like mosquito bites, but can also sometimes bruise or resemble a bullseye.

The term "*Babesia*" as used herein refers to a genus of parasitic protozoans including, but not limited to *Babesia bovis, Babesia microti, Babesia bigemina, Babesia divergens* etc, which affect vertebrates, including (though rarely) humans. Babesiosis is the disease caused by the *Babesia* parasite, and typically occurs in dogs, cattle, horses, and rodents. *Babesia* typically exhibit two life cycles: one in the invertebrate host (typically ticks) and one in the vertebrate host. Typical symptoms of babesiosis include fever, anemia, fatigue, aches, chills, red urine, and possibly death. Treatment is often unreliable or not available in the United States, and many of the medications available may cause severe side effects. Humans with babesiosis are usually treated with malaria remedies.

The term "protective tick antigen" as used herein, refers to an antigen that stimulates protective immunity to ticks. Protective immunity may be exhibited in a number of forms including but not limited to reduced or absent tick load due to failure of ticks to attach, death of ticks after or during feeding, prevention of ova production and death.

As used herein, the term "control" or "controlling" as in e.g., the phrase: "controlling ticks" or "controlling tick populations" or "controlling parasitic arthropods" or "controlling parasitic arthropod populations", refers to any means for preventing infection or infestation, reducing the population on already affected organisms, or elimination of the population of ticks or parasitic arthropods e.g. ticks, mosquitoes, lice fleas or other species whose "control" is desired. Indeed, "controlling" as used herein refers to any indica of success in prevention, elimination, reduction or amelioration of a parasitic arthropod population or parasitic arthropod problem.

The term "ameliorating" or "ameliorate" refers to any indicia of success in the treatment or control parasitic arthropods, including any objective or subjective parameter such as abatement, or diminution of parasitic arthropod populations or an improvement in a subject's physical well-being which may result from decreased load of ticks feeding upon a subject. Amelioration of parasitic arthropods e.g., ticks, can be based on objective or subjective parameters; including the results of a physical examination and/or total average parasite count.

The terms "isolated," "purified," or "biologically pure" as used herein, refer to material that is substantially or essentially free from components that normally accompany it as found in its native state. In an exemplary embodiment, purity and homogeneity are determined using analytical chemistry techniques such as polyacrylamide gel electrophoresis or high performance liquid chromatography. A protein that is the predominant species present in a preparation is substantially purified. In one exemplary embodiment, an isolated protective tick antigen nucleic acid is separated from open reading frames that flank the protective tick antigen gene and encode proteins other than the protective tick antigen. The term "purified" denotes that a nucleic acid or protein gives rise to essentially one band in an electrophoretic gel. Typically, it means that the nucleic acid or protein is at least 85% pure, at least 90% pure, at least 95% pure, or at least 99% pure.

The term "nucleic acid" as used herein, refers to a polymer of ribonucleotides or deoxyribonucleotides. "Nucleic acid" polymers typically occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The term "nucleic acid" also includes "recombinant nucleic acid". The term "recombinant nucleic acid" as used herein refers to a nucleic acid, not normally found in Nature that is typically formed in vitro using modern techniques of molecular biology. Thus, an isolated nucleic acid formed in vitro by ligating DNA molecules that are not normally joined, is an exemplary "recombinant nucleic acid".

The terms "polypeptide," "peptide" and "protein" are used interchangeably herein to refer to a polymer of amino acid residues. The terms apply to naturally occurring amino acid polymers and non-naturally occurring amino acid polymers as well as amino acid polymers in which one or more amino acid residues is an artificial chemical mimetic of a corresponding naturally occurring amino acid.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art (see, e.g., Creighton, Proteins (1984)). Such conservatively modified variants are in addition to and do not exclude polymorphic variants, interspecies homologs, and alleles.

The following eight groups illustrate some exemplary amino acids that are conservative substitutions for one another:
  1) Alanine (A), Glycine (G);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V);
  6) Phenylalanine (F), Tyrosine (Y), Tryptophan (W);
  7) Serine (S), Threonine (T); and
  8) Cysteine (C), Methionine (M)

Macromolecular structures such as polypeptide structures are described in terms of various levels of organization. For a general discussion of this organization, see, e.g., Alberts et al., Molecular Biology of the Cell ($3^{rd}$ ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "label" as used herein, refers to a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which antisera or monoclonal antibodies are available.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (e.g., 7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. In one exemplary embodiment, probes are directly labeled as with isotopes, chromophores, lumiphores, chromogens etc. In other exemplary embodiments probes are indirectly labeled e.g., with biotin to which a streptavidin complex may later bind. By assaying for the presence or absence of the probe, one can detect the presence or absence of the select sequence or subsequence.

Thus, the term "labeled nucleic acid probe or oligonucleotide" as used herein refers to a probe that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, over expressed, under expressed or not expressed at all.

The term "promoter" as used herein refers to an array of nucleic acid control sequences that direct transcription of a nucleic acid. As used herein, a promoter comprises necessary nucleic acid sequences near the start site of transcription, such as, e.g., a polymerase II type promoter, a TATA element. In some exemplary embodiments, a promoter also includes distal enhancer or repressor elements, which can be, but are not necessarily located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, a heterologous nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (e.g., 80% identity, preferably 85%, 90%, or 95% identity over a specified region) when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395 (1984).

Another example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10.degree. C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cased, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

I. Introduction:

In one exemplary embodiment, the invention provides a method for stably transfecting *Babesia* parasites. In one exemplary embodiment, stably transfected *Babesia* parasites expressing a heterologous nucleic acid encoding a tick protective antigen provides an effective vaccine system conferring immunological resistance to ticks.

In one exemplary embodiment, stably transfected *Babesia* parasites expressing a heterologous nucleic acid encoding a tick protective antigen are used to prepare live attenuated *Babesia* parasites for vaccination.

II. Constructing an Expression Vector for Transfection and Expression of Protective Antigens A. General Recombinant DNA Methods This invention utilizes routine techniques in the field of recombinant genetics. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, and/or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, Tetrahedron Letts. 22:1859-1862 (1981), using an automated synthesizer, as described in Van Devanter et. al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

B. Suitable Vectors

Development of stable targeted integration systems comprises identification of strong promoters, introducing and expressing foreign DNA, efficient selection markers, and the identification of regions of the *Babesia* genome that will make good targets for integration. The expression region of an exemplary expression vector suitable for preparing stably transfected *Babesia* parasites is shown in FIG. 1.

I. Promoters

Exemplary promoters for construction of expression vectors capable of expressing heterologus nucleic acids in stably transfected *Babesia* cell lines include, but are not limited to rap-1 (Suarez et al. (2004) Int. J. for Parasitology 34:1177-1184, which is incorporated herein by reference). The sequence of the rap-1 3' region used in the transfection vector are deposited in GenBank under the following accession number: AF027149. In another exemplary embodiment, the promoter comprises ef-1α. ef-1α is known in the art, see e.g., Suarez, C. E. et al (2006) Int. J. for Parasitology 36:965-973 which is incorporated herein by reference. The sequences for the ef-1α Promoter and ef-1α flanking regions that are used to construct an exemplary transfection vector were deposited in GenBank under this accession number: DQ322644.

Any suitable promoter can be used.

2. Selective Markers

Exemplary selectable markers include, but are not limited to the antifolate WR99210, puromycin and blasticidin. In one exemplary embodiment, blasticidin is the selective marker used. However, any suitable selectable marker known in the art can be used. Some exemplary markers are disclosed in e.g., Wel, A. et al. Mol Biochem Parasitol. 2004 March; 134(1):97-104; Mamoun, C. B. et al., Proc Natl Acad Sci USA. 1999 Jul. 20; 96(15):8716-20. Erratum in: Proc Natl Acad Sci USA 1999 Sep. 14; 96(19):10944; Wang, P. et al., Mol Biochem Parasitol. 2002 Aug. 7; 123(1):1-10.

3. Expressed Protective Antigens

Exemplary foreign antigens for eliciting protective immune responses include, but are not limited to Tick (*Boophilus microplus, Dermacentor* sp, etc.) antigens, *Anaplasma marginale, Babesia bigemina*, etc, Bm86, Bm95.

In one exemplary embodiment, the protective tick antigen present in the expression site of the expression vector is Bm86. Bm86 is known in the art, see e.g., U.S. Pat. No. 5,587,311; and Rand, K. N., et al. (1989) Proc Natl Acad Sci USA. December; 86(24):9657-61). An exemplary Bm86 nucleic acid sequence is provided in GenBank as accession number: I32386. In one exemplary embodiment, the protective tick antigen present in the expression site of the expression vector is at least about 90% identical to the sequence of Bm86 shown in GenBank accession number: I32386. In other exemplary embodiments, the protective tick antigen present in the expression site of the expression vector is at least about 91% identical, at least about 92% identical, at least about 93% identical, at least about 94% identical, at least about 95% identical, at least about 96% identical, at least about 97% identical, at least about 98% identical, at least about 99% identical, or at least about 100% identical to the sequence of Bm86 shown in GenBank accession number: I32386.

In an exemplary embodiment, the protective antigen is fused to a gfp-bsd fusion open reading frame used in the transfection vector shown in FIG. 1. In an exemplary embodiment, the gfp-bsd fusion open reading frame used in the transfection vector shown in FIG. 1 is amplified from vector pTracer-CMV/Bsd from InVitrogen bp 2576-3679. In some exemplary embodiments, gfp need not be present in the vector.

In another exemplary embodiment Bm95 provides a protective tick antigen. Bm95 is known in the art see e.g., Boue O, et al. Exp Appl Acarol. 2004; 32(1-2): 119-28.

Other exemplary protective antigens include, but are not limited to Bm91, which has regions of amino acid sequence similarity to angiotensin converting enzymes. Calreticulin (CRT) has been implicated in a wide variety of cellular processes and affected numerous biological and pathophysiological conditions. Therefore, CRT protein is an exemplary antigen against tick infestations. Serine protease inhibitors (Serpins) have a potential role of enzymatic regulatory inflammation mechanisms that are part of tick feeding mechanisms. Thus, in an exemplary embodiment Serpins are a protective tick antigen.

C. Cloning Methods for the Isolation of Nucleotide Sequences Encoding Protective Tick Antigens In general, the nucleic acid sequences encoding protective tick antigens and related nucleic acid sequence homologs are cloned from cDNA and genomic DNA libraries or isolated using amplification techniques with oligonucleotide primers by methods well known in the art. In an exemplary embodiment, protective tick antigen sequence are typically isolated from cDNA libraries comprising DNA sequences from *Boophilus microplus*. In one exemplary embodiment, antigens not normally involved in acquired resistance are isolated, cloned into an appropriate expression vector, transfected into *Babesia*, and are thus used to induce anti-tick immunity. In one exemplary embodiment, gut proteins e.g., Bm86, comprise protective tick antigens.

In an exemplary embodiment, DNA sequences which are similar to and/or homologous with the DNA coding for the tick protective antigens e.g., from *Boophilus microplus*, can be used to identify DNA sequences from other tick species by constructing cDNA or genomic DNA libraries for the other tick species and hybridizing *Boophilus microplus* DNA fragments to those libraries, and purifying recombinant organisms containing the DNA sequences hybridizing to the homologous genes.

D. Assays for Discovering Alternative Antigens

Antigens not normally involved in acquired resistance are exemplary protective tick antigens that can be used to induce anti-tick immunity using transgenic *babesia* vaccines. In an exemplary embodiment, these antigens are obtained from tick gut absorptive surface. Sera obtained from immunized animals can be used to identify antibody-reactive components of the resistance-inducing extract. Tick gut absorptive surface antigen glycoconjugates can be identified by lectin blotting, using a series of probes with different carbohydrate specificities by methods known in the art see e.g., Wikel S K. Vet Parasitol. 1988 September; 29(2-3):235-64.

In an exemplary embodiment, antibody-reactive components of the resistance-inducing extract are reverse cloned i.e., protein sequence is used to deduce nucleic acid sequence, so that probes can be synthesized and hybridized to libraries to obtain the gene encoding a new protective tick antigen.

III. Transfection Systems

The tick borne *Babesia* parasites are useful as live attenuated vaccines for control of *Babesia* parasites. Additionally, in an exemplary embodiment, *Babesia* parasites provide a convenient vector for the expression of antigens protective against ticks and other parasitic arthropods. Indeed, in one exemplary embodiment, vaccination with live attenuated *Babesia* parasites which have been transfected with protective tick antigens e.g., Bm86, Bm95, provides vaccine effective to protect the vaccinated animal against ticks as well as against *Babesia*.

In one exemplary embodiment, stable transfection of *Babesia bovis* is useful for introducing and expressing transgenes in *B. bovis* parasites that are used for preparing live *Babesia* attenuated strains that express foreign genes and thus, the foreign genes produce antigens that function as vaccines. In another exemplary embodiment, stable transfection of *Babesia bovis* is used to introduce and express markers that identify vaccinated animals.

Transfection of other parasitic organisms which affect vertebrate hosts and which require an intermediate arthropod vector can be used to prepare transgenic strains of the parasite, which express protective antigens against the arthropod. Exemplary parasitic organisms include but are not limited to *Plasmodium*, see e.g., Balu, B., and Adams, J. H. (2007) Int J. Parasitol. January; 37(1):1-10; and et al. (2004) Methods Mol. Biol. 270:263-76.

A. Transient Transfection

In an exemplary embodiment, *Babesia* strains are transiently transfected with genes encoding antigens protective against parasitic arthropods e.g., ticks. Transient transfection is known in the art, see e.g., Suarez et al. (2004) Int. J. for Parasitology 34:1177-1184.

B. Stable Transfection

In an exemplary embodiment, *Babesia* strains are stably transfected with genes encoding antigens protective against parasitic arthropods e.g., ticks. In an exemplary embodiment, expression vectors as disclosed in section II (above) are introduced into either *Babesia* infected erythrocytes or free merozoites.

In an exemplary embodiment, transfection is performed with a conventional electroporation system (BioRad GenePulser II). In another exemplary embodiment, transfection is performed with nucleofection technology (Amaxa). Typically, conventional electroporation is more effective for transfection of larger amounts of plasmid (100 µg range) whereas typically, nucleofection is more efficient for transfecting much smaller amounts (2 µg range), of circular or linearized plasmids.

In an exemplary embodiment, targets for gene substitution upon transfection are genes that are not needed for development of the parasite during its growth in in vitro cultures, although other genes may also be targeted. In one exemplary embodiment stable transfection is achieved using rap-1 and ef-1α genes as targets through homologous recombination. As is known in the art, double chain cuts delivered e.g., by restriction endonucleases, to homologus sequences located on the targeting (expression) vector direct recombination to sites in the genome homologus with the cut vector DNA (see e.g., Szostak, J. W. et al. (1983) Cell 33:25-35). In other exemplary embodiments, appropriate targets are identified using the *B. bovis* genome data and characterization of stage-specific transcripts. In one exemplary embodiment, 18s ribosomal units serve as target sequences, since the three *B. bovis* 18s ribosomal units can be differentially transcribed among distinct life stages of the parasite, with one of the genes not showing transcripts during in vitro merozoite culture stages. Thus, this region of the *B. bovis* genome can be targeted for integration without compromising parasite viability. In one exemplary embodiment *B. bovis* 18s ribosomal genes are used for preparing stable transfection constructs targeted to this region of the genome. In another exemplary embodiment, non-targeted integration is achieved using in transposons and pantropic retroviral vectors.

IV. Vaccinating Livestock

Live attenuated *Babesia* vaccines are known in the art see e.g., Callow, L. L. et al. (1997) Int. J. for Parasitology 27(7): 747-767; Anonymous. (1984) Immunization against bovine babesiosis. In: *Ticks and Tick-borne Disease Control. A Practical Field Manual*, Vol. II Chapter 10, pp 388-443 Food and Agriculture Organization, Rome; and de Waal, D. T., and Combrink, M. P. (2006) Vet Parasitol. May 31; 138(1-2):88-96. Epub 2006 Feb. 28. Review.

In one exemplary embodiment, *Babesia* parasites stably transfected with a heterologus nucleic acid capable of expressing a protective tick antigen, are used to prepare a live attenuated *Babesia* vaccine, by methods known in the art.

The live attenuated *Babesia* vaccine is administered to an animal, e.g., cattle, horse, dog, deer, goats, sheep, cats, pigs etc., in need thereof, by methods known in the art. In the animal, the protective tick antigen in the transgenic *Babesia* is expressed, thereby stimulating a protective immune response against the tick antigen and thus providing protective immunity against the tick ectoparasite.

In one exemplary embodiment, vaccination with transgenic *Babesia* induces permanent immunity, since animals infected with *Babesia* remain infected for life.

V. Testing for Immunization

In one exemplary embodiment the expression of molecular or antigenic tags on the expression vector are used for the identification and discrimination of vaccinated animals in the field. In an exemplary embodiment, the presence of antibodies or parasites in field animals is analyzed to determine whether these animals were naturally infected or previously vaccinated, for treatment or epidemiological purposes. Because transfected *Babesia* vaccine strains contain a gene that is not present in wild type strains, animals that have received the vaccine are readily identified by detection of the gene that is not present in wild type strains. In one exemplary embodiment, the gene not present in wild type strains is detected by PCR amplification. In another exemplary embodiment, the gene not present in wild type strains is expressed in the animal as an antigen which stimulates antibody production. Thus, vaccinated animals will elicit antibody responses against these expressed antigens, and these animals can also be identified using serological reactions, such as ELISA.

In another exemplary embodiment, the ability to detect, e.g., with PCR or immunological methods, animals vaccinated with transfected *Babesia* strains is useful for determining whether vaccine breakthroughs are due to the vaccine strain that reverted to virulence (not uncommon), or lack of protection of the vaccine strain against some virulent field strain due, for instance to antigenic variation.

In still another exemplary embodiment, vaccination with transfected *Babesia* vaccine strains permits tracking of the transmission of the vaccine strain to ticks or to other naïve animals via tick transmission. In one exemplary embodiment, the inclusion of the green fluorescent protein (gfp) gene in the transfection construct allow easy tracking by fluorescence microscopy of the localization of the vaccine strain in tick tissues, and in non-vaccinated animals. In other exemplary embodiments, tracking is facilitated by inclusion of any other expression of unique antigens in the vaccine strain, e.g., by PCR, immunological methods, immunofluorescence and/or in situ hybridization.

VI. Other Uses for a *Babesia* Stable Transfection System

The full sequence of the *Babesia* genome is now available, see e.g., Journal of Medical Entomology, Volume 43, Number 1, January 2006, pp. 9-16(8) and Brayton, K. A. et al. (2007) PloS Pathog. 3:1401-1413. Many of the sequenced genes are of unknown function. In one exemplary embodiment, a *Babesia* stable transfection system as disclosed herein, is useful for functional characterization of *Babesia* genes by permitting the construction of knock out strains. Knock out analysis of gene function is well appreciated by those of skill in the art. In one exemplary embodiment, a *Babesia* stable transfection system as disclosed herein, is useful for the characterization of *Babesia* promoters.

*Babesia bovis* and *Babesia bigemina* are important causative agents of bovine babesiosis in tropical and subtropical regions of the world. *Babesia divergens* is more common in temperate climates. Babesiosis was a significant problem in the southern US until the 1940's when it was controlled by eradication of the tick vectors by intensive acaricide dipping of cattle. However, the tick vectors are present in a buffer zone along the Rio Grande, in Mexico, and in US territories, and pose the threat of continual reemergence into the US as evidenced by occasional outbreaks of babesiosis in the border region. Emerging acaracide resistance of vector ticks in Mexico is a significant concern, since re-introduction of babesiosis into the US likely will occur via infected ticks. It is estimated that the first year cost of controlling vector ticks alone should they be introduced into the U.S. is over $1.3 billion. There is currently no babesial vaccine licensed for use in the U.S., and development of a vaccine is a high priority.

Thus, in one exemplary embodiment, a *Babesia* stable transfection system as disclosed herein, is useful for rational identification of subunit vaccine candidates for the development of a vaccine that is acceptable for use in the U.S. Indeed, in one exemplary embodiment, a *Babesia* stable transfection system is used to discover useful protective antigens which can be used directly as vaccines to protect against *Babesia* infection. In another exemplary embodiment, genes known to express useful protective antigens are cloned into an appropriate expression vector and stably transfected into *Babesia* for preparation of live attenuated vaccines to protect against further *Babesia* infection.

In another exemplary embodiment, the ability to stably transform *B. bovis* parasites provides a means for better understanding the biology of *Babesia* parasites by providing means for understanding parasite associated determinants of virulence, tick transmission, and immunity The following examples are offered to illustrate, but not to limit the invention.

EXAMPLES

Example 1

The following example illustrates exemplary methods for obtaining *Babesia* transfectants for use in the preparation of vaccines that protect against ticks and that may also protect against *Babesia*.

Materials and Methods

Parasites:

The Mo7 biological clone of *B. bovis* was derived by limiting dilution of the Mexico strain as described (Rodriguez et al, (1983) Infect Immun. 42:15-18; Hines et al. (1989) Mol. Biochem. Parasitol. 37: 1-10), and was maintained as a cryopreserved stabilate in liquid nitrogen (Palmer et al., (1982) Parasitology. 84:567-571). Parasites were grown in long term microaerophilous stationary-phase culture by previously described techniques (Levi and Ristic, (1980) Science. 207: 1218-1220; and Hines et al., (1989) supra). *B. bovis* purified merozoites were obtained from 8 to 10-flask expansion of *B. bovis* typically containing between 30-40% infected red blood cells (iRBC) as determined by microscopic counting of Giemsa stained slides, as described previously (Hines et al. (1992), Mol. Biochem. Parasitol. 55:85-94).

Plasmid Constructs:

Plasmid p4-35 encoding luciferase under the transcriptional control of the *B. bovis* ef-1α promoter (FIG. 2) was described previously (Suarez, C. E., et al., (2006) Int J. Parasitol. 36, 965-973, which is incorporated herein by reference). Plasmids were purified using the Qiagen endotoxin-free maxiprep kit (Qiagen Inc., CA) following the manufacturer's instructions.

Amaxa Nucleofection of Purified *Babesia bovis* Merozoites:

Varying amounts of plasmid (2 to 100 µg) suspended in 100 µl of Amaxa Nucleofactor reagent (Amaxa ByoSystems Inc.) were added to 10 µl of free merozoites (~2×10$^6$ free merozoites) mixed to avoid bubbles, and transferred to an 0.2 cm Amaxa electroporation cuvette. The cuvette was then placed in the Amaxa nucleofection device and nucleofected according to manufacturer's instructions using the Amaxa program v-024 in conjunction with the "*Plasmodium*" buffer. Immediately after nucleofection the cuvette contents were transferred to a culture well containing 1.1 ml of *Babesia* culture media with 10% normal RBCs. Transfected parasites were cultured in 24 well culture plates as described previously.

Electroporation:

Electroporation was performed in a Gene Pulser II apparatus (BioRad) using 0.2 cm cuvettes containing filter sterilized cytomix buffer (120 mM KCl, 0.15 mM CaCl$_2$, 10 mM K$_2$HPO$_4$/KH$_2$PO$_4$ pH 7.6, 25 mM HEPES pH 7.6, 2 mM EGTA, 5 mM McCl$_2$, final pH 7.6) at a final volume of 100 µl. Typically, 1-2×10$^6$ merozoites per cuvette were used for electroporation, except when indicated otherwise. Following electroporation, merozoites were cultured as described before for nucleofection.

Figure 1:
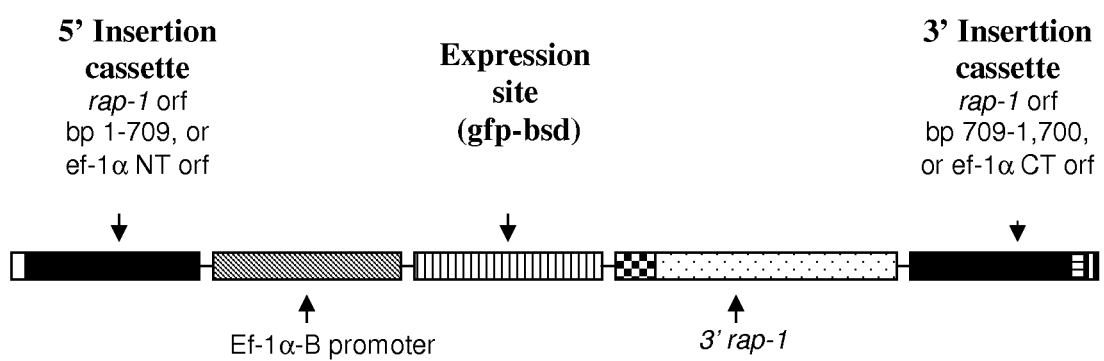
Figure 3A:
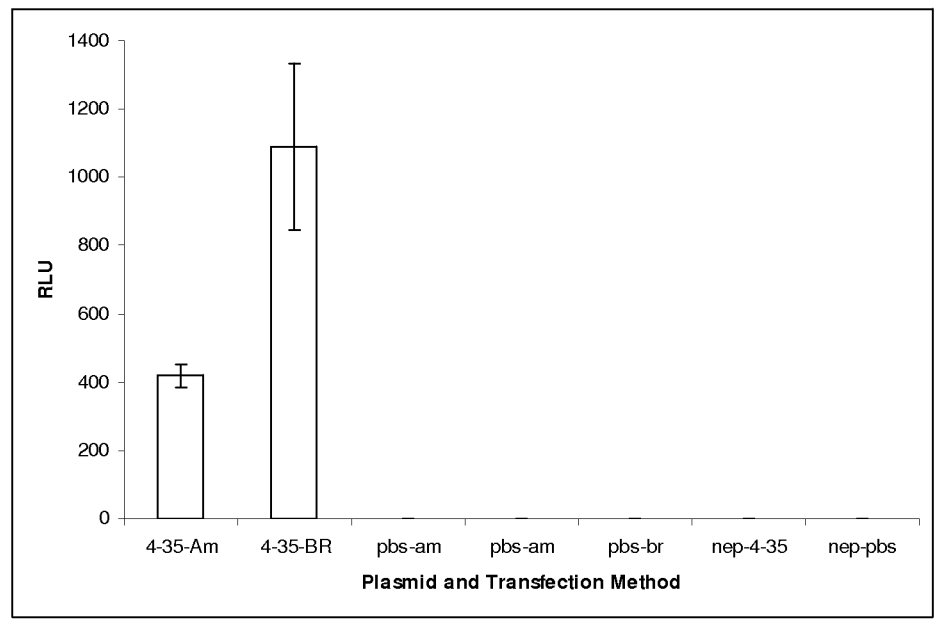
Figure 3B:
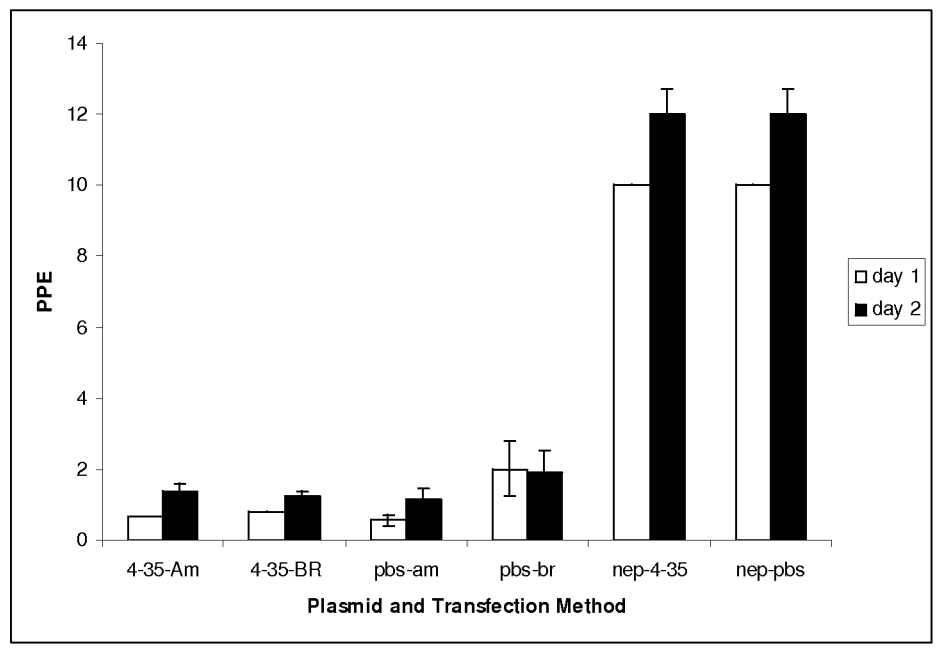

2. 5 Luciferase Assays:

Luciferase analysis was performed as described previously (Suarez et al., (2004) Int. J. Parasitol. 34, 1177-1184, which is incorporated herein by reference) using Promega's LAR II detection reagent at room temperature along with a Turner Designs TD-20/20 Tube Luminometer for a 10 second integration. For each set of luciferase assays, 2 µl of a 10$^{-6}$ dilution of Promega's QuantiLum Recombinant Luciferase diluted in 1× Passive Lysis Buffer was assayed as a standard Results and Discussion The above disclosed experiments compare the relative efficiency of the BioRad GenePulser II electroporation method (Suarez et al. (2006) supra) and the Amaxa nucleofection method (Balu et al. (2007) Int. J. Parasitol. 37: 1-10; Janse et al., (2006) Mol. Biochem. Parasitol. 145:60-70) for transfecting purified merozoites or infected erythrocytes with variable quantities of plasmid. p4-35-luc containing luciferase as a reporter gene under the control of the ef-1α promoters in the 5' region, and the 3' region of rap-1 (FIG. 1) (Suarez et al., (2006) supra). Thus, plasmid p4-35-luc or control pBS was first transfected into $10^8$ infected red blood cells (iRBC) containing about 30% iRBC parasitemia, with the Amaxa nucleofector to determine whether this device was suitable for the introduction of foreign plasmid DNA into infected red blood cells (iRBC) using the nucleofection settings that we previously determined for the transfection of purified merozoites (Suarez et al., 2007, manuscript submitted). The results of the Amaxa nucleofection of iRBC compared with BioRad electroporation performed on identical number of parasites using 100 µg of transfected plasmid are shown in FIG. 3. The luciferase values, measured 48 hours after transfection shown in FIG. 3A indicate that nucleofection also transfers plasmid DNA into iRBC, although it appears to be less efficient than electroporation at least in the settings tested in this experiment. In FIG. 3B shows the percentage of parasitized erythrocytes (PPE) in the first and second day after transfection. No differences in parasite viability were detected with this method when electroporation and nucleofection were compared. However, transfection resulted in decreased viability when the PPE of the transfected (either nucleofected or electroporated) with the non-transfected controls (nep 4-35 and nep-pBS) were compared.

Figure 4:
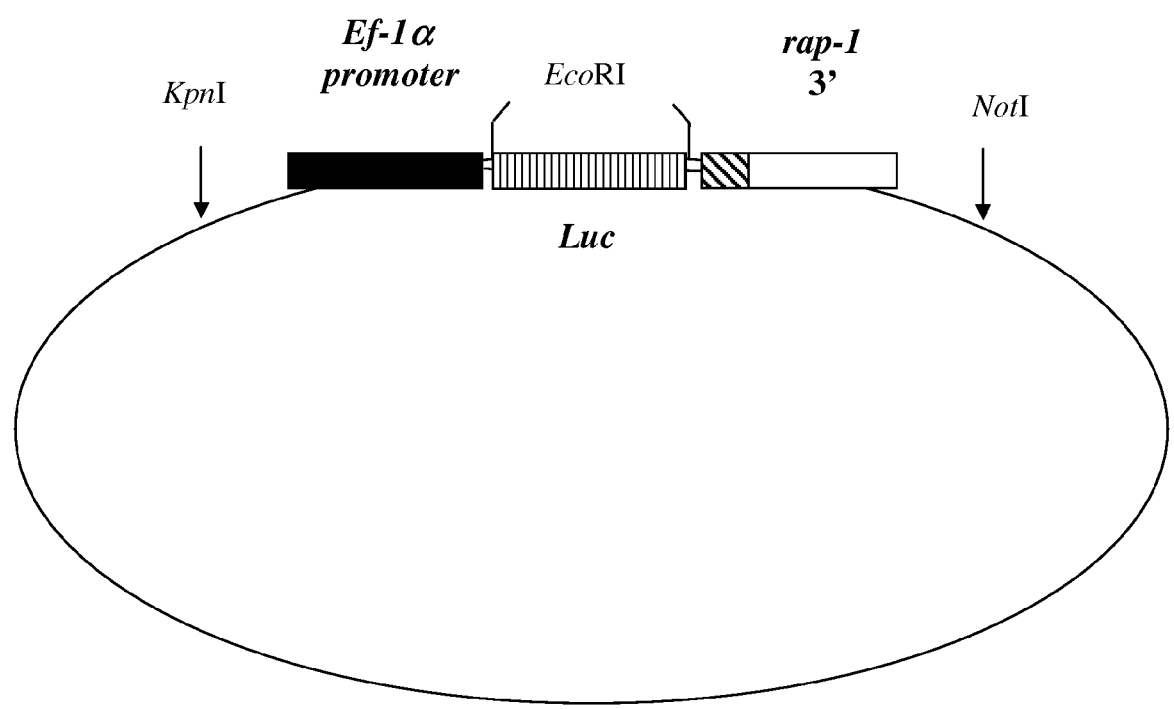

The efficiency of both transfection methods for transferring plasmid into iRBC was compared, as described above or into $10^6$ purified merozoites using either a large quantity of plasmid (100 µg) or a smaller quantity of plasmid (2 µg). Luciferase was measured at 24, 48 and 72 h, and the percentage of parasitized erythrocytes was also calculated as a parameter of viability. Parasites transfected with control plasmid pBS did not produce any significant luciferase activity. Overall, the data indicates that the peak of luciferase expression in transfected parasites occurs at 24 hours in all cases, and that the most efficient method of transfection tested in this study was electroporation of infected erythrocytes with 100 µg of plasmid, followed by nucleofection with 2 µg of plasmid. The data also confirms previous observations that nucleofection is more efficient than electroporation for transfecting small quantities of plasmids (2 µg range), whereas the inverse is true for transfection of larger quantities (100 µg range). Data in FIG. 4 shows a comparison of actual luciferase expression values expressed as RLU, in conjunction with the percentage of parasitized erythrocyte at 24, 48 and 72 hours after transfection. Data indicates that while the PPE increases, the RLU drops rapidly, consistent with the transient nature of the transfection. Similar growth patterns were observed in the four systems under study, therefore suggesting that a significant number of parasites remain viable after transfection regardless of the method used.

In summary, we demonstrated the feasibility of transfecting B. bovis infected erythrocytes by the method of nucleofection, and we also compared iRBC and purified merozoite transfection methods. The most efficient transfection method tested in this study uses 100 µg of plasmid on infected erythrocytes, but a very high rate of efficiency was also obtained using Amaxa nucleofection, which is the method of choice when using small quantities of plasmid for electroporation. This scenario is likely to occur when attempting transfection of restriction-enzyme linearized constructs to facilitate double cross-over integration mechanisms. Overall, these results illustrate stable transfection of exogenous DNA into Babesia parasites.

Example 2

The following example illustrates an exemplary method for the preparation Babesia parasites stably transfected with a heterologous nucleic acid. In one exemplary embodiment, stable transfection systems for Babesia are useful for functional analysis of the recently sequenced Babesia bovis genome (Brayton K. A., et al. supra). In addition, the ability stably transfect Babesia cells allows one of skill to knock out specific genes and to express transgenes. In exemplary embodiments stably transfected Babesia parasites are exploited for the development of attenuated Babesia vaccine strains co-expressing foreign genes as immunogens. In some exemplary embodiments, markers are also introduced into stable transfectant cell lines that can be used to identify vaccinated animals.

FIG. 4 illustrates the structure of plasmid p4-35-ef-luc. The restriction sites used for linearization (KpnI) and double digestion (KpnI and NotI) are indicated with arrows.

Nucleofection and electroporation systems for DNA transfections as disclosed above in Example 1, were used to transfect plasmid p4-35-ef-luc into Babesia merozoites. Plasmids were either circular, singly digested with KpnI or doubly digested with KpnI and NotI.

For restriction enzyme digestion, 10 µg of plasmid was digested with the indicated restriction enzyme (KpnI or NotI) following manufacturer's instructions. Both linearized (KpnI) or double digested (KpnI and NotI) plasmids were heated to 65° C. to inactivate the enzyme and then ethanol precipitated with sodium chloride and suspended to 2 µg/5 µl in sterile water. The completeness of digestion of plasmid DNA was confirmed by gel electrophoresis.

Plasmid p4-35-ef-luc was used to analyze if one transfection system would be more or less effective for transfection of 2 ∝g of circular plasmid, plasmid linearized with KpnI, or plasmid double digested with KpnI and NotI. The results indicate that luciferase expression from linear and the double digested plasmids were much lower when compared with circular plasmid using either transfection system. Nucleofection was markedly more efficient for transfecting restriction-digested DNA. No significant difference in post-transfection percentage parisitized erythrocytes (PPE) was observed among the three groups. The overall decrease in luciferase expression in the linear and the double-digested DNA when compared to circularized plasmid may be due to the increased stability of circular plasmid in the presence of parasite endogenous nucleases, a possible increased efficiency for transfection of the circular plasmid DNA, or a combination. In summary, results suggest that nucleofection is a method of choice for Babesia bovis merozoite transfection, when introducing smaller quantities of plasmid, or restriction digested DNA.

Example 3

The following example illustrates stable integration of plasmid DNA into the genome of Babesia bovis using blasticidin/blasticidin deaminase selection.

Blasticidin/blasticidin deaminase selection has been shown to work with other protozoa. Furthermore no known bsd gene is present in the B. bovis genome. Thus, the occurrence of resistant strains that are not transfected with the plasmid is reduced. Blasticidin proved to be an efficient inhibitor of the growth of B. bovis with an $IC_{50}$ of ~0.4 µg/ml, a drug concentration comparable to the $IC_{50}$ (0.35 µg/ml) calculated for Plasmodium falciparum parasites. In addition, a gfp/bsd fusion gene was used to incorporate an additional marker of expression. With this construct, blasticidin resistant parasites emerged relatively quickly after selection. The blasticidin-resistant transfected B. bovis parasites are able to grow in high concentrations of blasticidin with growth curves that are similar to non-selected parasites in the absence of blasticidin. Importantly, expression of the transfected gfp-bsd fusion protein in *B. bovis* is not toxic for the parasites, which have been able to strongly express the gfp-bsd protein at least nine months after electroporation.

The plasmid pgfp-bsd-ef was introduced into *B. bovis* infected erythrocytes by electroporation using several experimental strategies. These included circular, linearized and double digested plasmid in the presence or absence of the restriction enzyme NotI. It was previously reported that addition of NotI, or other restriction enzymes, in the transfection mix results in a 29-46 fold increase in transfection efficiencies, a technique known as restriction enhanced mediated integration (REMI) (Black et al., (1995) Mol. and Biochem Parasitol. 74: 55-63). In our experiments, transfectants able to grow in the presence of blasticidin were derived both in the presence and the absence of NotI. These transfectants are able to consistently express gfp-bsd for 9 months, consistent with stable expression. This suggests that the addition of NotI was not required for producing stable transformants.

Stable integration of the gfp-bsd gene into the *B. bovis* genome is supported by the following observations: 1) sustained growth in culture media containing concentrations of blasticidin that are otherwise inhibitory for wild type *Babesia,* 2) detection of fluorescence in transfected parasites more than 9 months after electroporation, 3) inability to recover plasmid in plasmid rescue experiments, 4) identification of gfp-bsd transcripts and expression of a gfp-bsd fusion protein in transfected merozoites, and 5) evidence of integration into the ef-1α locus in Southern blots and flanking PCR amplicons. Taken together, the experimental evidence demonstrates stable transfection of *B. bovis* parasites.

Materials and Methods

Parasites

The Mo7 biological clone of *B. bovis* was derived by limiting dilution of the Mexico strain as described (Rodriguez et al, (1983) Infect Immun. 42: 15-18; Hines et al. (1989) Mol. Biochem. Parasitol. 37, 1-10), and was maintained as a cryopreserved stabilate in liquid nitrogen (Palmer et al., (1982) Parasitology. 84: 567-571). Parasites were grown in long term microaerophilous stationary-phase culture by previously described techniques (Levi and Ristic (1980) Science. 207: 1218-1220; Hines et al., 1989 supra).

Blasticidin Inhibition

*B. bovis* parasites of the Mo7 strain were cultured in 1 ml cultures in 24 well plates containing 10% bovine red blood cells. Triplicate wells were cultured with or without increasing amounts of blasticidin added to the culture media at 0.15, 0.3, 0.6, 1.2, 1.5, 2.4, and 4.8 μg/ml, prepared from a 5 mg/ml stock solution of blasticidin (Invitrogen) in sterile water, for three consecutive days. Culture media was replaced daily. The percentage of parasitized erythrocytes (ppe) was estimated by microscopic counting of Diff-Quik (Dade Behring) stained slides as described (Suarez and McElwain, (2008) Exp Parasitol. 118: 498-504). Percentage *B. bovis* inhibition was calculated by dividing the mean ppe in triplicate blasticidin treated wells by the mean ppe in triplicate control wells grown in the absence of blasticidin, and multiplying by 100.

Plasmid Constructs

Plasmid pgfp-bsd-ef (FIG. 2 for diagrammatic representation) was derived from previously described plasmid p40-15-luc (Suarez et al., 2006 supra). The first 673 bps of the 5' region of the *B. bovis* ef-1α orf were amplified from *B. bovis* Mo7 genomic DNA using 6 primers Xho-EF-orf-F1 (5'-ctg acg ctc gag atg ccg aag gag aag act cac-3' SEQ ID NO:1) and Xho-EF orf-R1 (5'-cag ctg ctc gag atc tga tca agg gcc tcg acc-3' SEQ ID NO:2). The resulting 673 bp amplicon was digested with XhoI, and cloned into the XhoI site of plasmid p40-15-luc (Suarez et al., 2006, supra). The plasmid obtained was designated p40-15-luc-XhoI-ef-5'. The 673 bp of the 3' half of the *B. bovis* ef-1α orf were amplified from *B. bovis* Mo7 genomic DNA using primers Bam-EF-orf-F2: (5'-gca tcg gga tcc gga acc ccc aaa gag gcc cgt tg-3' SEQ ID NO:10) and Bam-EF-orf-R2: (5'-cta gca tcc tct tag cag cct ttt ggg cag ac-3' SEQ ID NO:11). The resulting 673 bp amplicon was digested with BamHI and cloned into the BamHI site of plasmid p40-15-luc-XhoI-ef-5'. This plasmid was designated p40-15-luc-XhoI-ef-5'-ef-3'BamHI. The gfp bsd fusion gene amplified from plasmid pTracer (Invitrogen) using primers Tracer-gfp-EcoI-F (5'-cgt cgt gaa ttc atg gcc tcc aaa gga gaa gaa c-3' SEQ ID NO:3) and Tracer-gfp-EcoI-R (5'-taa tgt gaa ttc gcc ctc cca cac ata acc aga g-3' SEQ ID NO:4) and digested with EcoRI was cloned into EcoRI-alkaline phosphatase treated plasmid p40-15-luc-XhoI-ef-5'-ef-3'BamHI, replacing the Luc gene. Finally, the resulting plasmid was modified to include an additional NotI site 3' to the XhoI insert by inserting the olinucleotide Apa-Not-Apa (5'-gcg gcc gcg gcc-3 SEQ ID NO:5) into the ApaI site, and the resulting construct was designated pgfp-bsd-ef. Plasmids were purified using the Qiagen endotoxin-free maxiprep kit (Qiagen Inc., CA) following the manufacturer's instructions. For NotI restriction enzyme digestion, 10 μg of plasmid was digested with the restriction enzyme following manufacturer's instructions. NotI digested plasmids were heated to 75° C. for 20 minutes to inactivate the enzyme and then ethanol precipitated with sodium chloride and suspended in 5 μl of sterile water. The completeness of digestion of plasmid DNA was confirmed by gel electrophoresis.

Electroporation of *Babesia bovis* Infected Erythrocytes and Drug Selection

*B. bovis* infected erythrocytes from an 8 flask expansion were centrifuged at 400×g in a table-top centrifuge for at 5 minutes to pellet the erythrocytes. The cell pellet was washed one time in filter sterilized cytomix buffer (120 mM KCl, 0.15 mM $CaCl_2$, 10 mM $K_2HPO_4/KH_2PO_4$ pH 7.6, 25 mM HEPES pH 7.6, 2 mM EGTA, 5 mM $MgCl_2$, final pH 7.6) and centrifuged again as before. Electroporation was performed in a Gene Pulser II apparatus (BioRad) using 0.2 cm cuvettes containing 62.5 μl filter sterilized cytomix plus the digested plasmid and 37.5 μl of washed *B. bovis* infected red blood cells to a final volume of ~100 μl. Typically, $1\text{-}2\times10_8$ infected erythrocytes per cuvette were used for electroporation. The electroporator settings used were 1.2 kv/25 μF/200 ohms (Suarez and McElwain, 2008, supra). The experimental protocol for transfection is summarized in Table I.

Briefly, infected erythrocytes were electroporated with 20 μg of circular plasmid or plasmid linearized with NotI, in the presence or absence of NotI enzyme in the cuvette (Black et al., 1995 supra). Control cultures contained either circular or NotI linearized plasmid without NotI enzyme. In total, this resulted in 12 different experimental parameters (Table I). Following electroporation, infected erythrocytes were cultured as described above. For blasticidin selection, a 5 mg/ml blasticidin stock solution was prepared and stored at −80° C. Blasticidin was added to the culture media at concentrations as indicated in the Results section, starting 24 hrs after electroporation. The ppe was calculated daily as described above. Parasites growing in moderate blasticidin concentration in culture wells from experimental parameters 1 and 2 (Table 1) were combined and subjected to high concentration blasticidin selection to obtain parasite line 1-2-124 (see below, Results).

TABLE 1

Experimental protocol for electroporation of plasmid pgfp-bsd-ef into the Mo7 strain of *B. bovis*.

| Plasmid and format | NotI added to cuvette | Actual voltage (Kv) | Time constant (sec) | Blasticidn Selection (µg/ml) |
|---|---|---|---|---|
| 1. Circular pgfr-bsd-ef | − | 1.31 | 0.32 | 0.6* |
| 2. Circular pgfp-bsd-ef | − | 1.24 | 0.26 | 0.3* |
| 3. Circular pgfp-bsd-ef | + | 1.26 | 0.52 | 0.6* |
| 4. Circular pgfp-bsd-ef | + | 1.31 | 0.38 | 0.3 |
| 5. NotI-digested pgfp-bsd-ef | − | 1.33 | 0.28 | 0.6 |
| 6. NotI-digested pgfp-bsd-ef | + | 1.26 | 0.58 | 0.3* |
| 7. NotI-digested pgfp-bsd-ef | + | 1.31 | 0.34 | 0.6* |
| 8. NotI-digested pgfp-bsd-ef | + | 1.31 | 0.32 | 0.3* |
| 9. pBS-circular | − | 1.24 | 0.3 | 0.6 |
| 10. pBS-circular | − | 1.26 | 0.56 | 0.3 |
| 11. Linear pBS (NotI digested) | − | 1.31 | 0.32 | 0.6 |
| 12. Linear pBS (NotI digested) | − | 1.28 | 0.5 | 0.3 |

*Experiments in which blasticidin-resistant transfectants were identified.

Characterization of Putative Stably Transfected Parasite Line 1-2-124

Following transfection and blasticidin selection, a parasite line designated 1-2-124 (see below, Results) was analyzed in detail to confirm correct expression of the gfp-bsd fusion protein and integration into the chromosome. This parasite line was followed temporally using fluorescence microscopy, reverse transcriptase PCR, and Western blot to confirm continuous expression of the gfp-bsd gene. Southern blots, direct PCR and sequence analysis were used to examine and genetically characterize chromosomal integration.

Genetic Characterization

*B. bovis* merozoite total RNA from parasite line 1-2-124 (see below, Results) was extracted from in vitro cultures by the standard TRIzol (Life Technologies) procedure as described previously (Suarez et al. (2003) Mol Biochem Parasitol. 127:101-12), and treated with RNAse-free DNAse (Ambion). For RT PCR, Superscript First Strand Synthesis System kit (BRL-Invitrogen) was used to generate cDNA with 1 µg of total RNA from cultured parasites. Reactions were carried out as per the manufacturer's recommendation for first-strand synthesis using an Oligo(dT) primer. The full size gfp-bsd orf was amplified either from genomic DNA or from cDNA using the Gold Taq Polymerase kit (Applied Biosystems) and the specific primers Tracer-gfp-EcoI-F and Tracer-gfp-EcoI-R (see above). Products of RT-PCR were cloned into vector pCR 2.1 (Invitrogen) and sequenced. Genomic DNA was extracted from cultured merozoites by the standard phenol-chloroform procedure. For Southern blot analysis, genomic DNA from *B. bovis* merozoites was digested with restriction enzyme BglII, electrophoresed, transferred to ZetaProbe Nylon membranes, and hybridizations carried out as previously described (Suarez et al., 2003, supra). Digoxigenin-labeled probes representing the complete gfp-bsd and ef-1α orf's were prepared by PCR amplification using a PCR Dig-Probe Synthesis kit as recommended by the manufacturer (Boehringer-Roche). The gfp-bsd probe was prepared by PCR amplification of plasmid pTracer (InVitrogen) with primers gfp-bsd-f (5-atg gcc tcc aaa gga gaa gaa c-3' SEQ ID NO:6), and gfp-bsd-r (5'-gcc ctc cca cac ata acc aga g-3' SEQ ID NO:7). The r5-r6 amplicon was obtained by PCR amplification of genomic DNA of the parasite line 1-2-124 with the set of primers ef-rev5 (5'-cat atc aag ctt ctt taa cgg gat gac ata tat g-3' SEQ ID NO:8) and ef-rev6 (5'-gac cat aag ctt agt aaa cga tag aac aga cta ag-3'SEQ ID NO:9). The amplicon was cloned into plasmid vector pCR 2.1 (Invitrogen) and sequenced in full by standard techniques.

Immunoblot Analysis

To confirm the expression of correctly sized gfp-bsd fusion protein, merozoites of parasite line 1-2-124 were subjected to SDS-PAGE and analyzed by western blot. Immunoblots were performed as described previously (Suarez et al., 2003 supra) using anti-GFP antibody (Invitrogen) at a dilution of $1:10_4$, and goat anti rabbit-immunoglobulin peroxidase conjugate (Life Biosciences).

Results

Growth of *Babesia bovis* is Inhibited by Blasticidin in In Vitro Cultures:

Previous unsuccessful attempts to stably transform *B. bovis* utilized DHFR-induced resistance to pyrimethamine or WR99210 for selection of transfected lines (Gaffar et al., 2004 Mol. Biochem. Parasitol. 133:209-19). Natural resistance to these drugs developed rapidly in culture (Gaffar et al., 2004, supra). To determine whether *B. bovis* growth could be inhibited with blasticidin, and to estimate the concentration of blasticidin appropriate for establishing a blasticidin/blasticidin deaminase (bsd) transfection system, *B. bovis* Mo7 strain parasites were cultured in the presence of varying concentrations of blasticidin ranging from 0 to 5 µg/ml in triplicate wells. The percentage of parasitized erythrocytes (ppe) in each well was determined for the first three days after splitting the cultures in each well to a starting ppe of 0.5%. The results obtained in the third day of blasticidin selection indicate that *B. bovis* is sensitive to blasticidin. No *B. bovis* infected erythrocytes could be detected in stained slides after three days in culture using a blasticidin dose of 5 µg/ml. The 50% inhibitory concentration of blasticidin ($IC_{50}$) after three days of drug selection was determined to be 10~0.4 µg/ml, and a concentration of blasticidin in the 0.64-1.25 µg/ml range resulted in negligible parasite growth. Subsequent stable transfection experiments were performed using either 0.3 or 0.6 µg/ml blasticidin.

Initial Characterization of *Babesia bovis* Infected Erythrocytes after Transfection:

Plasmid pgfp-bsd-ef was designed with ef-1α orf insertion sequences at the 5' and 3' regions to target integration of the gfp-bsd cassette into the ef-1α locus. The construct was introduced into *B. bovis* Mo7 infected erythrocytes by electroporation as either circular plasmid, or as gel-purified NotI linearized plasmid in the presence or absence of the restriction enzyme NotI in the electroporation cuvette (Table 1) (Black et al. 1995 supra). Circular pBS plasmid was used in control cultures. Blasticidin selection was initiated using either 0.3 or 0.6 µg/ml of blasticidin starting 24 hours after electroporation. Parasite counts were performed daily and the percentage of parasitized erythrocytes calculated.

Blasticidin resistant parasites emerged as early as five days after electroporation under selection with 0.3 or 0.6 µg/ml of blasticidin (Table 1). No blasticidin resistant parasite lines emerged in cultures containing parasites electroporated with the control pBS plasmid (Table 1). Blasticidin resistant *B. bovis* parasites were present in cultures established after electroporation in the presence or absence of NotI using either circular or linearized plasmids. Due to their early emergence and rapid rate of growth in otherwise inhibitory concentrations of blasticidin, cultures derived after electroporation with circular plasmid in the absence of NotI (experiments 1 and 2, Table 1) were further studied.

To select for highly blasticidin resistant lines, parasites were cultured in either 0.64 µgml or 2.0 µg/ml of blasticidin. A parasite line designated 1-2-124 was able to grow in a blasticidin concentration of 2.0 µg/ml, reaching almost 4.0% ppe two days after splitting of the cultures.

The parasite line 1-2-124 was further maintained in culture under blasticidin selection and subjected to 1:10 splitting every four days. Transfected parasites emitted high levels of gfp fluorescence while fluorescence was never detectable in control transfected parasites. Total DNA was extracted from this parasite line 21 days after the start of the blasticidin selection, and analyzed by PCR using primers that amplify the full size gfp-bsd fusion orf. A ~1.1 kb band, compatible with the size of the gfp-bsd fusion orf, was obtained after amplification of the transfected 1-2-124 parasite line DNA (data not shown). Sequencing of this amplicon demonstrated 100% sequence identity with the gfp-bsd fusion orf present in plasmid pTracer (Invitrogen). To initially determine whether plasmid was still present in 1-2-124, 1 µg of this DNA was used for plasmid rescue experiments by transforming competent *E. coli* cells after electroporation. No bacterial colonies were obtained after transformation and ampicillin selection of *E. coli* competent cells at one month following transfection, suggesting that the gfp-bsd amplicon was not amplified from pgfp-bsd-ef or other plasmid DNA. Plasmid indistinguishable from pgfp-bsd-ef was recoverable from culture of another line at the same time point. These results suggested that the transfection plasmid was integrated into the chromosome of parasite line 1-2-124 and that gfp-bsd was consistently expressed in the presence of blasticidin. Thus line 1-2-124 was characterized more extensively.

Analysis of Parasite Line 1-2-124

Line 1-2-124 parasites growing either in the presence or the absence of blasticidin selection were able to consistently express a fluorescent product over a period of 9 months after electroporation (at which time routine fluorescent microscopy analysis was discontinued). To confirm expression from the fusion gene the production of a gfp-bsd transcript and gfp-bsd fusion protein were examined. A gfp-bsd transcript was consistently present in transfected *B. bovis* after RT-PCR analysis using primers that amplify approximately 1,200 bp of the orf. Expression of a gfp fusion protein was demonstrated by Western blot analysis of parasite line 1-2-124 using monospecific polyclonal antibody against gfp. Rabbit anti-gfp antibodies bound a protein of ~46 kD, compatible with the expected size of the gfp-bsd fusion protein. Anti-gfp antibody did not react with any protein in wild type Mo7 strain parasites. An additional band of approximately 70 kD was present in immunoblots of parasite line 1-2-124 but not in control Mo7 parasites. The identity of this protein is unknown. However, its presence only in transfected parasites suggests that it is either a dimer of gfp-bsd, or a second fusion protein originating from an unexpected gfp integration event.

Growth characteristics of the blasticidin selected parasite line 1-2-124 were examined and compared with mock pBS-transfected control parasites in the presence or absence of 6.4 µg/ml blasticidin. Representative growth curves are shown in FIG. 5A. The results indicate that parasite line 1-2-124 is able to grow at similar rates with or without addition of blasticidin at a concentration 10 times higher (6.4 µg/ml) than used for original selection, while control parasites transfected with pBS were not able to grow in the presence of blasticidin at 6.4 µg/ml. In addition, no differences were observed between growth rates of parasite cell line 1-2-124 and control parasites in the absence of blasticidin.

The gfp-bsd Gene is Integrated into the ef-1α Locus of Parasite Cell Line 1-2-124:

Overall, the results suggest that a gfp-bsd gene is integrated into the genome of the *B. bovis* transfected line 1-2-124. Southern blot analysis using ef-1α and gfp-bsd specific dig-labeled probes was used to confirm this, and to determine the location of the gfp bsd gene in the *B. bovis* genome. Parasite DNA was digested with the restriction enzyme BglII, which cuts twice outside the ef-1α a locus of the *B. bovis* genome, but not within the transfection cassette. This digest should generate a fragment of 12,431 bp containing the ef-1α locus in wild type parasites. In control Mo7 strain blots, a genomic restriction fragment of the predicted size hybridizes with the ef-1α probe, but not with the gfp-bsd probe. There is an upward shift of the main hybridization band in the parasite line 1-2-124 using the ef-1α specific probe, consistent with an expected increase in the size of the BglII fragment containing the ef-1α locus in the transfected cell line. The gfp-bsd probe hybridized with a restriction fragment of the same size as the ef-1α probe, but only in the transfected cell line. Southern blot analysis showed no evidence of episomal DNA containing the gfp-bsd gene. The lack of episomal plasmids and the upward shift of the ef-1α restriction fragment that hybridizes with both ef-1α and gfp-bsd probes strongly suggests that the exogenous gfp-bsd gene is inserted into the targeted ef-1α gene locus.

To further confirm and localize integration of the gfp-bsd gene into the ef-1α locus, amplicons were generated by PCR using the forward primer ef-rev-6 targeted to sequence unique to the intergenic region of the ef-1α locus in wild type parasites, but not present in the transfection plasmid, and the reverse primer efrev-5 representing sequences in the ef-1α promoter of the gfp-bsd gene of the transfection vector pbsd-gfp-ef. The two primers used in this amplification are separated by ~600 bp in the genome of the wild type Mo7 strain, but are oriented in the same strand in *B. bovis* and thus are unable to generate any amplicon from wild type parasites. Amplification of genomic DNA obtained from the transfected line 1-2-124 with this set of primers resulted in a 1.5 kb band, which was cloned into 2.1 topo vector and fully sequenced. No PCR product was obtained either from the plasmid pgfp-bsd-ef or from wild type Mo7 genomic DNA using this set of primers. Analysis of the 1.5 kb PCR product indicated that it contains sequence from the genome that is not present in the plasmid and sequence unique to the plasmid that includes plasmid associated restriction sites. The absence of the XhoI restriction site present in plasmid pgfp-bsd-ef suggests that it originated from the genomic version of the gene. In contrast, the 3' end of the r5-r6 amplicon includes the sequence of primer xho-ef-orf-r1 exactly as it is present in the transfection construct. The results indicate that the 1.5 kb amplicon contains a chimera generated as a product of homologous recombination between the genome and the transfection plasmid.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A genetically modified *Babesia bovis* parasite comprising a stably transfected heterologous nucleic acid, wherein the heterologous nucleic acid comprises a nucleic acid sequence encoding a protective tick antigen selected from the group consisting of the Bm86 of *Boophilus microplus*, the Bm91 of *Boophilus microplus*, and the Bm95 of *Boophilus microplus*.

2. A genetically modified, live attenuated *Babesia bovis* parasite comprising a stably transfected heterologous nucleic acid, wherein the heterologous nucleic acid comprises a nucleic acid sequence encoding a protective tick antigen selected from the group consisting of the Bm86 of *Boophilus microplus*, the BM95 of *Boophilus microplus*, and the BM91 of *Boophilus microplus*.

3. A genetically modified, live attenuated *Babesia* parasite comprising a stably transfected heterologous nucleic acid, wherein the stably transfected heterologous nucleic acid comprises a nucleic acid sequence that encodes for a tick protective antigen, wherein the protective tick antigen is selected from the group consisting of the BM86 of *Boophilus microplus*, the BM95 of *Boophilus microplus*, and the BM91 of *Boophilus microplus*, the genetically modified, live attenuated *Babesia* parasite made according to a method of stably transfecting a *Babesia* parasite, the method comprising:

(i) preparing an expression vector comprising the heterologous nucleic acid, a targeting sequence, and a selectable marker, (ii) cutting the expression vector with at least one restriction endonuclease, thereby providing a cut expression vector, (iii) transfecting the cut expression vector into merozoites of the *Babesia* parasite or red blood cells infected with the *Babesia* parasite using nucleofection or electroporation, or a combination thereof, and (iv) selecting for the *Babesia* parasite expressing a phenotype associated with the expression of the selectable marker, thereby providing the genetically modified, live attenuated *Babesia* parasite.

4. The genetically modified, live attenuated *Babesia* parasite of claim 3, wherein the *Babesia* parasite is *Babesia bovis*.

5. The genetically modified, live attenuated *Babesia* parasite of claim 3, wherein the targeting sequence is a gene that is not needed by the *Babesia* parasite for growth in in-vitro culture.

6. The genetically modified, live attenuated *Babesia* parasite of claim 3, wherein the expression vector is cut with the at least one restriction endonuclease prior to the transfection of the expression vector into the merozoites of the *Babesia* parasite or prior to the transfection of the red blood cells infected with the *Babesia* parasite.

7. A vaccine comprising the genetically modified, live attenuated *Babesia bovis* parasite of claim 4, wherein the vaccine is capable of stimulating an anti-tick immune response specific to the protective tick antigen in an animal.

8. The vaccine of claim 7, wherein the protective tick antigen encoded is the Bm86.

9. A vaccine comprising the genetically modified, live attenuated *Babesia bovis* parasite of claim 2, wherein the vaccine is capable of stimulating an anti-tick immune response specific to the protective tick antigen in an animal.

10. A composition comprising the genetically modified *Babesia bovis* parasite of claim 1.

* * * * *

UNITED STATES PATENT AND TRADEMARK OFFICE
CERTIFICATE OF CORRECTION

PATENT NO. : 9,265,818 B2  
APPLICATION NO. : 12/114988  
DATED : February 23, 2016  
INVENTOR(S) : Carlos E. Suarez and Donald P. Knowles, Jr.

It is certified that error appears in the above-identified patent and that said Letters Patent is hereby corrected as shown below:

Title page, Column 1, under "Assignees", change "Washington State University Research Foundation, Pullman, WA (US)" to "Washington State University, Pullman, WA (US)"

Signed and Sealed this  
Thirty-first Day of May, 2016

Michelle K. Lee  
*Director of the United States Patent and Trademark Office*

SEQUENCE LISTING

<160> NUMBER OF SEQ ID NOS: 11

<210> SEQ ID NO 1
<211> LENGTH: 33
<212> TYPE: DNA
<213> ORGANISM: Artificial Sequence
<220> FEATURE:
<223> OTHER INFORMATION: Primer

<400> SEQUENCE: 1
ctgacgctcg agatgccgaa ggagaagact cac          33

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
cagctgctcg agatctgatc aagggcctcg acc          33

<210> SEQ ID NO 3
<211> LENGTH: 34
<212> TYPE: DNA
<213> ORGANISM: Artificial Sequence
<220> FEATURE:
<223> OTHER INFORMATION: Primer

<400> SEQUENCE: 3
cgtcgtgaat tcatggcctc caaaggagaa gaac         34

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
taatgtgaat tcgccctccc acacataacc agag         34

<210> SEQ ID NO 5
<211> LENGTH: 12
<212> TYPE: DNA
<213> ORGANISM: Artificial Sequence
<220> FEATURE:
<223> OTHER INFORMATION: Primer

<400> SEQUENCE: 5
gcggccgcgg cc                                 12

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
atggcctcca aaggagaaga ac                      22

<210> SEQ ID NO 7
<211> LENGTH: 22
<212> TYPE: DNA
<213> ORGANISM: Artificial Sequence

```
<220> FEATURE:
<223> OTHER INFORMATION: Primer

<400> SEQUENCE: 7
gccctcccac acataaccag ag                                               22

<210> SEQ ID NO 8
<211> LENGTH: 34
<212> TYPE: DNA
<213> ORGANISM: Artificial Sequence
<220> FEATURE:
<223> OTHER INFORMATION: Primer

<400> SEQUENCE: 8
catatcaagc ttctttaacg ggatgacata tatg                                  34

<210> SEQ ID NO 9
<211> LENGTH: 35
<212> TYPE: DNA
<213> ORGANISM: Artificial Sequence
<220> FEATURE:
<223> OTHER INFORMATION: Primer

<400> SEQUENCE: 9
gaccataagc ttagtaaacg atagaacaga ctaag                                 35

<210> SEQ ID NO 10
<211> LENGTH: 35
<212> TYPE: DNA
<213> ORGANISM: Artificial Sequence
<220> FEATURE:
<223> OTHER INFORMATION: Primer

<400> SEQUENCE: 10
gcatcgggat ccggaacccc caaagaggcc cgttg                                 35

<210> SEQ ID NO 11
<211> LENGTH: 32
<212> TYPE: DNA
<213> ORGANISM: Artificial Sequence
<220> FEATURE:
<223> OTHER INFORMATION: Primer

<400> SEQUENCE: 11
ctagcatcct cttagcagcc ttttgggcag ac                                    32
```